US010744225B2

(12) United States Patent
Lindgren et al.

(10) Patent No.: US 10,744,225 B2
(45) Date of Patent: Aug. 18, 2020

(54) FOAMED SILICONE IN WOUND CARE

(71) Applicant: Mölnlycke Health Care AB, Gothenburg (SE)

(72) Inventors: Lars Lindgren, Gothenburg (SE); Dennis Hansson, Gunnilse (SE); Shiva Eibpoosh, Gothenburg (SE)

(73) Assignee: MÖLNLYCKE HEALTH CARE AB, Gothenburg (SE)

( * ) Notice: Subject to any disclaimer, the term of this patent is extended or adjusted under 35 U.S.C. 154(b) by 350 days.

(21) Appl. No.: 15/753,581

(22) PCT Filed: Aug. 24, 2016

(86) PCT No.: PCT/EP2016/069963
§ 371 (c)(1),
(2) Date: Feb. 20, 2018

(87) PCT Pub. No.: WO2017/032790
PCT Pub. Date: Mar. 2, 2017

(65) Prior Publication Data
US 2019/0001019 A1     Jan. 3, 2019

(30) Foreign Application Priority Data

Aug. 26, 2015   (EP) .................................... 15182571

(51) Int. Cl.
*A61F 13/00*     (2006.01)
*A61L 26/00*     (2006.01)
(Continued)

(52) U.S. Cl.
CPC .... *A61L 26/0085* (2013.01); *A61F 13/00017* (2013.01); *A61F 13/00025* (2013.01);
(Continued)

(58) Field of Classification Search
None
See application file for complete search history.

(56) References Cited

U.S. PATENT DOCUMENTS 4,550,125 A * 10/1985 Lee .................... C08L 83/04
521/117
2013/0310780 A1 * 11/2013 Phillips .................. A61P 17/00
604/319

FOREIGN PATENT DOCUMENTS

WO     WO-2012/001371 A1     1/2012

OTHER PUBLICATIONS

International Search Report and Written Opinion dated Nov. 28, 2016 by the International Searching Authority for Patent Application No. PCT/EP2016/069963, which was filed on Aug. 24, 2016 and published as WO 2017/032790 on Mar. 2, 2017 (Inventor-Lindgren et al.; Applicant—Mölnlycke Health Care AB) (16 pages).

* cited by examiner

*Primary Examiner* — Kim M Lewis
(74) *Attorney, Agent, or Firm* — Ballard Spahr LLP

(57) ABSTRACT

A silicone foam is described that is produced in-situ at a wound site, e.g. in a wound cavity, through a multi-component system, based on a physical foaming process, wherein the gas required to form the foam structure is provided through a blowing agent independently of the curing reaction of polyorganosiloxane components of the multi-component system. Therefore, the blowing agent is provided as a distinct entity of the multi-component system that is, in particular, not the result of any chemical reaction taking place in the multi-component system. A device for producing the foam and the corresponding negative pressure wound therapy kit are also described.

22 Claims, 2 Drawing Sheets

(51) Int. Cl.
*C08J 9/00* (2006.01)
*C08J 9/14* (2006.01)
*C08L 83/04* (2006.01)
*C08K 5/56* (2006.01)
*C08L 83/00* (2006.01)
*A61M 1/00* (2006.01)
*C08G 77/12* (2006.01)
*C08G 77/20* (2006.01)

(52) U.S. Cl.
CPC .... *A61F 13/00068* (2013.01); *A61L 26/0019* (2013.01); *A61L 26/0052* (2013.01); *A61M 1/0088* (2013.01); *C08J 9/008* (2013.01); *C08J 9/0052* (2013.01); *C08J 9/0061* (2013.01); *C08J 9/0095* (2013.01); *C08J 9/141* (2013.01); *C08J 9/142* (2013.01); *C08K 5/56* (2013.01); *C08L 83/00* (2013.01); *C08L 83/04* (2013.01); *C08G 77/12* (2013.01); *C08G 77/20* (2013.01); *C08J 2201/022* (2013.01); *C08J 2201/026* (2013.01); *C08J 2203/12* (2013.01); *C08J 2203/14* (2013.01); *C08J 2203/16* (2013.01); *C08J 2203/182* (2013.01); *C08J 2205/05* (2013.01); *C08J 2207/10* (2013.01); *C08J 2383/05* (2013.01); *C08J 2383/07* (2013.01); *C08J 2483/05* (2013.01); *C08J 2483/07* (2013.01)

FOAMED SILICONE IN WOUND CARE

CROSS-REFERENCE TO RELATED APPLICATIONS

This application is a U.S. National Phase Application of International Application No. PCT/EP2016/069963, filed Aug. 24, 2016, which claims priority to European Application No. 15182571.8, filed Aug. 26, 2015, each of which are hereby incorporated by reference in their entirety.

FIELD OF THE INVENTION

The present invention relates to a multi-component system for producing a silicone foam, a device for producing a silicone foam, and a corresponding negative pressure wound treatment kit.

BACKGROUND OF THE INVENTION

Some wounds, such as pressure or diabetic ulcer wounds, or surgically created wounds, form a cavity in a patient's body. It may be desirable to fill the wound cavity, for example as part of a course of treatment. Various types of wound dressings or pads are used to fill wound cavities. These wound dressings or pads must be fitted for the particular wound size and shape, which can vary greatly. Some such dressings are easily conformable to the size and shape of the particular wound being treated. For example, gauze may be used as a cavity wound filler. As a further example, MELGISORB™ (produced by Molnlycke Health Care) is a soft, sterile calcium sodium alginate dressing that is used to fill wound cavities.

In some wound care applications, it may be desirable to use a wound pad made of a less conformable material. For example, porous and semi-rigid polymer foams are often used as wound fillers during negative pressure wound treatment. These materials may offer the advantage of allowing fluid channels through themselves even when subjected to negative pressure. Without wishing to be bound by any particular theory, it is also thought that the mechanical interaction between these more rigid materials and the wound may contribute to wound healing processes. The suitability of such less conformable materials notwithstanding, these dressings or pads can be difficult to size and shape to fit a wound. Such pads are typically supplied in one of several standard sizes and shapes, which then must be individually altered, typically with a utensil such as scissors.

A foam produced in situ in a wound cavity has particular advantages in the use as a wound filler as the produced foam can conform and adapt to a given shape of a wound cavity. Examples of foam material that can be used as in situ formed wound filler include polyurethane foam, and silicone foam such as Cavi-Care™. In such known foam materials, the foam is generally produced by mixing liquid components, e.g. pre-polymer, in the wound cavity, wherein the components react to cross-link, which reaction in turn releases the gas (e.g. carbon dioxide in case of a polyurethane foam and hydrogen gas in case of Cavi-Care™), which is required to form the foam cells.

One problem of these known foaming systems, which can also be described as "chemical foaming" systems, is that the foaming process is dependent on the reaction rate of the curing reaction (which reaction leads to the formation of the gas necessary to form the pore structure). Said reaction rate cannot be allowed to be too fast nor too slow, in order to achieve a desirable, e.g. open-cell, foam structure. Thus, it may be difficult to control the overall foaming process. Consequently, the foaming process is typically relatively slow, and it can thus be difficult to estimate how much material is required for a given wound cavity as the foam continues to form over several minute and may rise up over the edge of the wound cavity and spread out laterally onto the peri-wound area, long after a given amount of foam components was mixed in the cavity, which effects clearly are not desirable. Another problem with a relatively slow foaming process is that the unreacted (liquid) components may flow out from the cavity site, in particular in case the cavity is located on a difficult to dress area and/or on a vertical surface of the body.

WO 2012/001371 discloses a method and apparatus for providing a wound filler at a wound site prior to the application of negative pressure wound therapy, the method of WO'371 comprising: securing at least one drape element over a wound site, and subsequently injecting filler material through at least one opening in the drape. Thereby, the risk of excess foam on the peri-wound area, as discussed above, can be reduced. However, the solution provided in WO'371 is complicated and requires the use of drape which can be undesirable as such a drape, inter alia, limits the possibility of visual inspection and control of the cavity (which can often have complex 3D form) when filling it up with foam material. Also, excess foam material still may flow out from the opening in the drape.

Hence, there is a need in the art to provide a device for producing a foam having improved control of the foaming process and/or avoiding at least one of the disadvantages as discussed above.

SUMMARY OF THE INVENTION

In view of the above-mentioned and other drawbacks of the prior art, one object of the present invention is to provide a silicone foam in-situ at a wound site, which foam and which process for providing a foam in-situ does not suffer from the disadvantages outlined above or at least minimizes the disadvantages.

According to a first aspect of the invention, these and other objects are achieved through a multi-component system for producing a foam, said system comprising:
  a first component comprising a first polyorganosiloxane, said first polyorganosiloxane comprising at least two silicon-bonded hydrogen atoms;
  a second component comprising a second polyorganosiloxane, said second polyorganosiloxane comprising at least two alkenyl- and/or alkynyl groups, and at least one hydrosilylation catalyst;
  said multi-component system further comprising at least one blowing agent.

The general concept underlying the present invention is based on the realization that a silicone foam may be produced in situ at a wound site, e.g. in a wound cavity, through a multi-component system, based on a physical foaming process, wherein the gas required to form the foam structure is provided through the blowing agent independently of the curing reaction of the polyorganosiloxane components of the multi-component system.

Therefore, in accordance with the present invention, the blowing agent is provided as a distinct entity of the multi-component system that is, in particular, not the result of any chemical reaction taking place in the multi-component system.

As a consequence of the fact that the gas used to create the pore structure of the silicone foam, i.e. the blowing agent, is provided separately and independently of the curing reaction, said curing reaction may be adapted to be rapid such that cell walls of the foam structure, provided through the blowing agent, are essentially instantly stabilized. Accordingly, the overall foaming process of the multi-component system may be adapted to be much faster than in the known "chemical foaming" processes, wherein the blowing agent is provided by, and thus dependent on, the curing reaction. The faster foaming process thus achieved through the multi-component system provides inter alia improved control of the final size of the foam, wherein size control is a known problem associated with the slower chemical foaming process, especially when applied in situ in a wound cavity.

In accordance with the present invention, the blowing agent is the main source for the gas that leads to the formation of foam. Further in accordance with the present invention, the reaction between the first component and the second component essentially does not lead to the production of gas that leads to or aids in the formation of foam.

In embodiments of the invention, the first component comprises a first polyorganosiloxane comprising at least three silicon-bonded hydrogen atoms, and the second component comprises a second polyorganosiloxane comprising at least two alkenyl- and/or alkynyl groups.

In accordance with the present invention, the terms 'number of silicon-bonded hydrogen atoms' and the 'number of alkenyl- and/or alkynyl groups' refers to an average number of atoms/groups per polyorganosiloxane molecule.

In embodiments of the invention, the first component comprises a first polyorganosiloxane comprising at least two silicon-bonded hydrogen atoms, and the second component comprises a second polyorganosiloxane comprising at least three alkenyl- and/or alkynyl groups.

The inventors have realized that, in order to ensure a fast curing reaction in the multi-component system, it may be advantageous that either (i) the total number of silicon-bonded hydrogen atoms in the multi-component system are in excess of the total number of alkenyl and/or alkynyl groups in the multi-component system, wherein the polyorganosiloxanes comprising the silicon-bonded hydrogen atoms, e.g. the first polyorganosiloxane, preferably have a lower average molecular weight than the polyorganosiloxanes comprising the alkenyl and/or alkynyl groups, e.g. the second polyorganosiloxane; or (ii) the total number of alkenyl and/or alkynyl groups in the multi-component system are in excess of the total number of silicon-bonded hydrogen atoms in the multi-component system, wherein the polyorganosiloxanes comprising the alkenyl and/or alkynyl groups, e.g. the second polyorganosiloxane, preferably have a lower average molecular weight than the polyorganosiloxanes comprising the silicon-bonded hydrogen atoms, e.g. the first polyorganosiloxane. Without wishing to be bound by theory, it is believed that these ratios/values enable the smaller polyorganosiloxanes comprising the functional groups, which are present in excess, to have a greater mobility in the reaction mixture of the multi-component system, than the larger polyorganosiloxanes comprising the functional groups in deficit, which overall is believed to enhance the reaction rate of the curing reaction.

In embodiments of the invention, the ratio between the total number of silicon-bonded hydrogen atoms and the total number of alkenyl and/or alkynyl groups, in the multi-component system, is between 2 and 20, for example, between 4 and 16 or between 6 and 10, such as 8.

In embodiments of the invention, the number average molecular weight of the first polyorganosiloxane is less than the number average molecular weight of the second polyorganosiloxane.

In embodiments of the invention, the first polyorganosiloxane has a number average molecular weight of 500 to 6000 g/mol, and wherein the second polyorganosiloxane may have a number average molecular weight of 10 000 to 150 000 g/mol.

In embodiments of the invention, the ratio between the total number of alkenyl and/or alkynyl groups and the total number of the silicon-bonded hydrogen atoms, in the multi-component system, is between 2 and 20, for example, between 4 and 16 or between 6 and 10, such as 8.

In embodiments of the invention, the number average molecular weight of the second polyorganosiloxane is less than the number average molecular weight of the first polyorganosiloxane.

In some embodiments, the second polyorganosiloxane has a number average molecular weight of 500 to 6000 g/mol, and wherein the first polyorganosiloxane may have a number average molecular weight of 10 000 to 150 000 g/mol.

The inventors have also realized that since the gas required for pore formation is provided separately/independently from the curing reaction, said curing reaction between the first and the second polyorganosiloxane can proceed faster in the present 'physical foaming' process than in 'chemical' foaming and, as a consequence, the amount of catalyst can be chosen to be higher than in the 'chemical' foaming processes known form the art. In embodiments of the invention, the at least one hydrosilylation catalyst may comprise a platinum complex, or complexes of any other suitable transition metal complex, including, in particular, complexes of ruthenium, rhodium, palladium or osmium, among others.

In some embodiments, the at least one hydrosilylation catalyst comprises a divinyl tetramethyl disiloxane-platinum (0)-complex or a methyl vinyl cyclosiloxane-platinum(0)-complex. In embodiments of the invention, the total concentration of platinum in the in the multi-component system may be more than 50 ppm, for example, more than 100 ppm. In some embodiments, the total concentration of platinum in the in the multi-component system may be between 50 and 300 ppm. In some embodiments, the total concentration of platinum in the in the multi-component system may be between 50 and 200 ppm, for example, between 50 and 150 ppm or between 100 and 200 ppm.

In embodiments of the invention, the second polyorganosiloxane has the following general formula representing a statistical copolymer

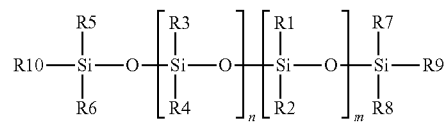

wherein R1 is selected from monovalent or functionally substituted C4-C12 hydrocarbon groups,
wherein R2 is selected from monovalent or functionally substituted C1-C12 hydrocarbon groups,
wherein R3 to R10, independently, are selected from monovalent or functionally substituted C1-C3 hydrocarbon groups, and wherein at least one of R3 to R10 is a C2-C3 alkenyl or C2-C3 alkynyl, and wherein n and m indicate the number of repeating units, wherein n and m, independently, are at least one, preferably greater than 5, and wherein the ratio between the total number of m and n preferably is from 1:100 to 40:100, for example, from 3:100 to 30:100, such as from 5:100 to 25:100.

In a preferred embodiment R3 to R10, independently, are selected from monovalent or functionally substituted C1-C3 hydrocarbon groups, resulting in a total of at least two C2-C3 alkenyl or C2-C3 alkynyl hydrocarbon groups per molecule, with n and m as defined above.

In embodiments of the invention, R1 is selected from the group consisting of C5-C12 aryl, for example phenyl or diphenyl, C4-C12 alkyl, C4-C12 alkenyl, C4-C12 alkynyl, and C4-C12 alkoxy, and wherein R2 is selected from the group consisting of C1-C12 alkyl, C2-C12 alkenyl, C2-C3 alkynyl, C1-C3 alkoxy, and C5-C12 aryl.

In embodiments of the invention, R1 is selected in from the group consisting of C5-C12 aryl, for example phenyl or diphenyl, C4-C12 alkyl, C4-C12 alkenyl, C4-C12 alkynyl, and C4-C12 alkoxy, and wherein R2 is selected from the group consisting of C1-C3 alkyl, C2-C3 alkenyl, C2-C3 alkynyl, and C1-C3 alkoxy, for example methyl, ethyl, propyl, methoxy, ethoxy, propoxy group. For example, R1 may be a phenyl wherein R2 may be a methyl or ethyl.

In embodiments of the invention, R1 and R2, are independently selected from the group consisting of C5-C12 aryl, for example phenyl or diphenyl, C4-C12 alkyl, C4-C12 alkenyl, C4-C12 alkynyl, and C4-C12 alkoxy. For example, R1 and R2 may be a phenyl.

In embodiments of the invention, R3 to R10 are independently selected from the group consisting of C1-C3 alkyl, C2-C3 alkenyl, C2-C3 alkynyl, and C1-C3 alkoxy, for example methyl, ethyl, propyl, methoxy, ethoxy, propoxy group.

In embodiments of the invention, R9 and R10 are C2 alkenyl groups.

In embodiments of the invention, R3 to R8 are methyl groups.

In embodiments of the invention, R1 and R2 are phenyl groups.

In embodiments of the invention, the blowing agent has a boiling point of less than 25° C. For example, the blowing agent may have a boiling point of less than 20° C. or less than 10° C., such as less than 5° C. or less than 0° C. In embodiments of the invention, the blowing agent has a boiling point of between −50 to 25° C., for example between −50° C. to 10° C. such as between −40° C. to 0° C. Thus, the blowing agent is advantageously in a gaseous form when the multiple-component system is applied to a wound site at normal conditions, in particular at room or at skin temperature and under normal atmospheric pressure (i.e. ca. 101.3 kPa); thereby the blowing agent enables foam cell formation when the first and second components are mixed and cured.

In embodiments of the invention, the blowing agent comprises a compound selected from the group consisting of propane, butane, isobutane, isobutene, isopentane, dimethylether or mixtures thereof. In some embodiments, the blowing agent comprises a compound that is inert. In accordance with the present invention, the term "inert" should be understood as pertaining to a compound that is not able to participate in a chemical reaction with any one of the compounds comprised in the first or second components, in any significant way.

In embodiments of the invention, the blowing agent is comprised in the first and/or second component. For example, in some embodiments, the blowing agent may be substantially dissolved in the first and/or the second component. In further embodiments of the present invention, the blowing agent is provided as a separate component and comes into contact with the first and/or second component only when the components are released.

In embodiments of the invention, the first and/or second component further comprise(s) at least one colloidal or pyrogenic silica.

In embodiments of the invention, the viscosity of the first and second components, independently, ranges from 5000 to 50000 mPa s (cP). In some embodiments, the viscosity of the first and second components, independently, ranges from 10000 to 30000 mPa s (cP), for example, from 15000 to 25000 mPa s (cP), such as about 20000 mPa s (cP).

In embodiments of the invention, the viscosity of the first and the second component is substantially the same. Thereby, the mixing of the first and second component may be facilitated. For example, in case a propellant gas is used to bring the first and the second components in contact with each other, for example by means of applying an elevated pressure on the first and second deformable containers containing the first and second components, respectively, it is advantageous that the viscosity of the first and second components is substantially the same to ensure that release rate of the components is even so that a desirable degree of mixing can be achieved.

In embodiments of the invention, the first component may further comprise the second polyorganosiloxane. By properly adjusting the ratio between first and second polyorganosiloxane, the viscosity of the first component and the second component may be adapted to be substantially the same.

In embodiments of the invention, the first component may further comprise a third polyorganosiloxane comprising at least one silicon-bonded hydrogen atom or at least one alkenyl- and/or alkynyl group.

In embodiments of the invention, the second component may further comprise a fourth polyorganosiloxane, wherein the fourth polyorganosiloxane comprises at least one alkenyl- and/or alkynyl group.

In embodiments of the invention, the onset and/or progress, including the termination, of the in-situ curing process of a multi-component silicone foam is monitored.

When, for example, the first and the second component of a multi-component system as described above are applied, for example from a deformable container, respectively, onto a wound, it sometimes may be difficult or cumbersome to monitor the proper dispensing of both components, in particular in a ratio that allows for optimal curing.

Therefore, in embodiments of the invention, the onset and/or progress, including the termination, of the in-situ curing process of the multi-component silicone foam is monitored by tracking the emptying of the container, in which the first and second component, respectively, is contained, for example by way of measuring the gauge on a container and/or by measuring the volume of a deformable container.

In other or additional embodiments, the onset and/or progress, including the termination, of the curing process of a multi-component silicone foam is monitored by adding at least one dyestuff to the first and second component, respectively, wherein the at least one dyestuff for the first component is of different color compared to the at least one dyestuff of the second component and wherein the cured foam has a resulting color that is different from the color of both components, respectively.

In accordance with the present invention, the term 'different' color refers to a $\Delta E^*_{ab}$ (also called $\Delta E^*$, dE*, dE, or "Delta E") value as defined in *International Commission on Illumination* (CIE) standard of 1994 (known as "CIE94") of at least 10, preferably at least 20, further preferably at least 30. In preferred embodiments, the color of one component is a hue of blue while the color of the other component is a hue of yellow, wherein the mixed and progressively cured silicone foam then exhibits an evolving hue of green.

In accordance with these embodiments, the practitioner applying the components to a wound cannot only check that both components are and have been dispensed properly, but can also monitor the progress and termination of the curing process.

In embodiments of the invention, the dyestuff is selected from dyes, colorants, pigments and the like.

According to a second aspect of the invention, the abovementioned and other objects are achieved by means of providing a device for producing a foam, said device comprising the multi-component system according to the invention, and at least one means for bringing the first component and the second component in contact with each other, wherein the first component and the second component are contained separately.

In embodiments of the invention, the device comprises a first deformable container containing the first component, and a second deformable container containing the second component, and at least one means for bringing the first component and the second component in contact with each other. For example, the at least one means for bringing the first component and the second component in contact with each other may be a propellant gas.

The term "deformable container" should, in accordance with the present application, be understood as a container that is capable of adapting its form and shape to the material contained therein and/or to an external pressure applied thereon. For example, a conceivable "deformable container" may be made of a flexible plastic material, e.g. a plastic pouch, wherein such plastic material is gas and liquid impermeable. Accordingly, in embodiments of the invention, the deformable container may be a sealed plastic pouch with a controllable opening.

In embodiments of the invention, the device comprises a first deformable container containing the first component and a second deformable container containing the second component, wherein the first and/or the second components may comprise the blowing agent, and/or wherein the device may comprise a third container containing the blowing agent.

In embodiments of the invention, the at least one means for bringing the first component and the second component in to contact with each other is a propellant gas, for example a propellant gas that is present in between the two containers, which ensures or aids, by virtue of being at higher pressure than ambient pressure, that the components present in the two containers are released into the intended wound site, after opening of the controllable opening(s)

The propellant gas may be identical to or different from the blowing agent as described above. In accordance with the present invention, it is conceivable that one and the same gas performs the functionality of the blowing agent (which is to ensure or aid that a foam structure is achieved instantly upon release and mixing of the first and the second component) and the functionality of the propellant gas (which is to ensure or aid that the components present in the two containers are released into the intended wound site, after opening of the controllable opening).

In some embodiments the propellant gas comprises a compound selected from the group consisting of nitrogen, oxygen or carbon dioxide. In embodiments of the invention, the propellant gas is nitrogen. In some embodiments the propellant gas comprises a compound selected from the group consisting of propane, butane, isobutane, isobutene, isopentane, dimethylether or mixtures thereof.

In embodiments of the invention, the device comprises a spray dispenser comprising the multi-component system, a discharge valve and a mixing nozzle. In some embodiments, the spray dispenser may be a metallic or plastic container.

In embodiments of the invention, the spray dispenser comprises a first deformable container containing the first component and a second deformable container containing the second component, wherein the first and/or the second components may comprise the blowing agent, and/or wherein the spray dispenser may comprise a third container containing the blowing agent.

In embodiments of the invention, the at least one means for bringing the first component and the second component in to contact with each other is a propellant gas that is present between the first and second deformable containers and an interior surface of the spray dispenser. Thereby, the spray dispenser may be pressurized by the propellant gas such that, when the spray dispenser is triggered in use, for example by means of opening a controllable opening, the first and the second components, in their respective deformable containers, are released substantially simultaneously and the deformable containers can be emptied at substantially the same rate, thus achieving a desirable mixing of the first component and the second component.

In embodiments of the invention, the device comprises a first chamber containing the first component and a second chamber containing the second component, wherein the first and the second chambers are separated from each other, wherein the first and/or the second components may comprise the blowing agent.

In embodiments of the invention, the device comprises a spray dispenser comprising a controllable opening that is discharge valve and a mixing nozzle, wherein the spray dispenser comprises the first and second chambers, and wherein the at least one means for bringing the first component and the second component in to contact with each other is the blowing agent comprised in the first component and/or second component.

As discussed above, the blowing agent of the multi-component system according to the invention is an essential feature to ensure that a foam structure is achieved when the first and the second components are mixed and applied to a surface. However, in some embodiments of the device, the blowing agent may also function as a means to bring the first and second components in contact with each other.

In embodiments of the invention, the blowing agent is substantially dissolved in the first component and/or the second component. For example, the deformable containers or chambers, discussed above, may be provided with the blowing agent under elevated filling pressure. For example, the deformable containers or chambers may be have an applied pressure of at least 1.5 bar.

In embodiments of the invention, the blowing agent is selected such that the solubility of the blowing agent in the first and/or the second component is at least 3% w/w at a filling pressure of at least 1.5 bar at a temperature of 20° C. Thereby, a sufficient foaming, upon mixing the first and second components, may be achieved.

In embodiments of the invention, the concentration of the blowing agent in the first and/or second components, independently, is from 1 to 40% w/w, for example from 5 to 30% w/w or from 5 to 20% w/w, such as from 10 to 15% w/w.

According to a third aspect of the invention, the abovementioned and other objects are achieved through a silicone foam obtained or obtainable from the multi-component system according to the invention.

In embodiments of the invention, the silicone foam comprises at least a partially open pore structure. For example, the silicone foam may comprise a mixture of closed cells and open cells. In some embodiments, the silicone foam may comprise at least one channel that reaches from a first external surface of the silicone foam to a second external surface of the silicone foam, wherein the at least one channel comprises a plurality of coherent open cells. Thereby, a fluid may be transported from the first external surface to the second external surface through said at least one channel.

In some embodiments, the first or second external surface comprise a continuous film of cross-linked silicone.

In embodiments of the invention, the silicone foam has a density of less than 0.7 kg/m$^3$, for example less than 0.6 kg/m$^3$ or less than 0.5 kg/m$^3$, such as less than 0.4 kg/m$^3$.

In embodiments of the invention, the silicone foam has a density of from 0.1 to 0.6 kg/m$^3$, for example from 0.2 to 0.5 kg/m$^3$ or from 0.2 to 0.4 kg/m$^3$, such as about 0.3 kg/m$^3$.

In embodiments of the invention, the silicone foam is hydrophilic.

In accordance with the present invention, the term "hydrophilic" refers to the water-permeability of a material or the water-attracting capabilities of a molecule or a surface, e.g. a surface of a porous structure. In the context of a material with pores (such as, for example, a foam including open-cells) or materials with through-holes, such a material is "hydrophilic" if the material takes up water. In the context of a material without pores or any through-holes, such a material is considered "hydrophilic" if it does not resist the flow of water into or through the material. For example, hydrophilicity of a material can be tested using a water column of up to one inch height exerting pressure on the material for at least 60 minutes, at least 90 minutes, or at least 24 hours. The term "resisting" flow is to be understood to mean that any flow of water into or through the foam in such a test is so low that it is below a given detection limit for the test.

According to a fourth aspect of the invention, the abovementioned and other objects are achieved through the use of the multi-component system or the device or the silicone foam, according to the invention, in wound care, in particular in negative pressure wound therapy.

According to a fifth aspect of the invention, the abovementioned and other objects are achieved through a negative pressure wound therapy kit comprising:
 a negative pressure source for providing negative pressure to a wound;
 the multi-component system according to the invention for providing a silicone foam in a wound cavity;
 a film dressing comprising a plastic film to be applied on the silicone foam, to cover and substantially seal the wound from the surrounding environment.

In embodiments of the invention, the negative pressure wound therapy kit further comprises a conduit configured to transmit negative pressure from the negative pressure source to the film dressing, thereby providing a negative pressure in and around the wound.

According to a sixth aspect of the invention, the abovementioned and other objects are achieved through a method of treating a wound comprising the step of:

providing a multi-component system according to the invention;
 in-situ producing and curing a silicone foam within the wound cavity, such that the produced silicone foam is in physical contact with substantially the entire area of the wound cavity;
 providing a film dressing on a top surface of the silicone foam and on the skin surrounding said wound cavity skin, to thereby provide a substantially air-tight seal over the wound;
 providing a negative pressure source for providing negative pressure to a wound;
 providing a conduit configured to transmit negative pressure from the negative pressure source to the film dressing; and
 connecting the conduit to the negative pressure source.

In some embodiments of the invention, the silicone foam is produced essentially only with the blowing agent that is part of the multi-component system according to the invention, and essentially without any gas formed as a result of the reaction between the first component and the second component.

BRIEF DESCRIPTION OF THE DRAWINGS

These and other aspects of the invention will now be shown in more detail, with reference to the appended drawings showing an exemplary embodiment of the invention, wherein.

DESCRIPTION OF EXAMPLE EMBODIMENTS OF THE INVENTION

In the following description, exemplary embodiments of the present invention are described, with reference to the accompanying drawings.

Figure 1:
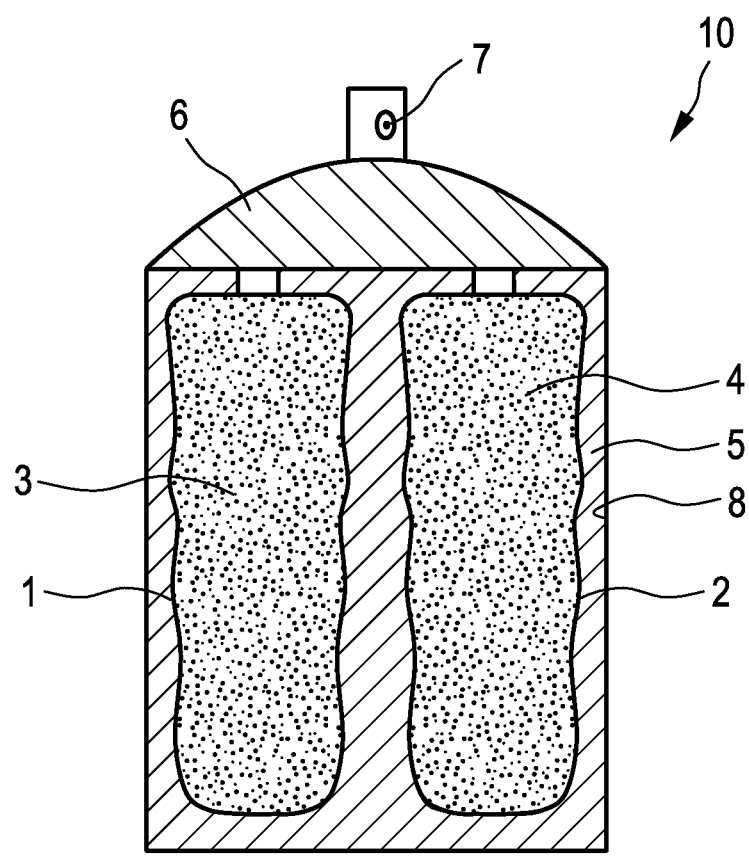
FIG. 1 is a cross-sectional view of an embodiment of a device according to the invention.

FIG. 1 illustrates an exemplary embodiment of a device for producing a foam, comprising a multi-component system comprising: a first component comprising a first polyorganosiloxane comprising at least two silicon-bonded hydrogen atoms; a second component comprising a second polyorganosiloxane comprising at least two alkenyl- and/or alkynyl groups and at least one hydrosilylation catalyst; and at least one blowing agent.

As illustrated in FIG. 1, the device may be realized as a spray dispenser 10 comprising a first deformable container 1 containing the first component 3 and a second deformable container 2 containing the second component 4. The first deformable container 1 and the second deformable container 2 may be realized as plastic pouches, which are gas and liquid impermeable and which have controllable opening.

In some embodiments, for example as depicted in FIG. 1, the spray dispenser 10 comprises a mixing nozzle 6 and a discharge valve 7, wherein the first deformable container 1 and second deformable container 2 are connected, and sealed, to the mixing nozzle 6. The spray dispenser device 10 further comprises a propellant gas 5, as a means for bringing the first component 3 and the second component 4 in contact with each other, which propellant gas 5 is present between the first 1 and second 2 deformable containers and an interior surface 8 of the spray dispenser 10. Thus, when the spray dispenser 10 is triggered, the propellant gas 5 can facilitate an optimal mixing of the first component 3 and second component 4.

Further, at least one of the first component 3 and the second component 4 comprises a blowing agent that is substantially dissolved therein. For example, the first deformable container 1 containing the first component 3 and/or the second deformable container 2 containing the second component 4 may typically be provided with the blowing agent at an elevated pressure of at least 1.5 bar, wherein the blowing agent may be selected such that its solubility in the first component 3 and/or in the second component 4 is at least 3% w/w at 20° C. The concentration of the blowing agent in the first component 3 and/or the second component 4 may advantageously be from 5 to 20% w/w, such as from 10 to 15% w/w.

The blowing agent advantageously has a boiling point of less than 25° C. For example, the blowing agent may have a boiling point of less than 20° C. or less than 10° C., such as less than 5° C. or less than 0° C. In embodiments of the invention, the blowing agent may have a boiling point of between −50 to 25° C., for example between −50° C. to 10° C. such as between −40° C. to 0° C.

In some embodiments, the blowing agent comprises a compound selected from the group consisting of propane, butane, isobutane, isobutene, isopentane, dimethylether or mixtures thereof. In some embodiments, the blowing agent advantageously comprises a compound that is inert in the sense that it does not react with any chemical or compound, nor does it interfere with the curing reaction between, the first component 3 and the second component 4.

Thus, by (i) selecting a blowing agent that has a boiling point below the normal temperature of use, e.g. skin temperature or room temperature, that is, by means of selecting a blowing agent that is gaseous outside the spray dispenser 10; and by (ii) properly adjusting the concentration of the blowing agent in the first component 3 and/or the second component 4, in the respective pressurized deformable containers, the blowing agent may instantly provide a foam structure in the mixture of the components, i.e. upon first mixing the first component 3 and the second component 4 and applying the mixture on a surface, e.g. on a skin surface or in a wound cavity, which foam structure is then rapidly stabilized ('frozen') as the first component 3 and the second component 4 cure to provide a permanent structure around the foam's cavities.

In some embodiments, the viscosity of the first component 3 and the second component 4, independently, ranges from 5000 to 50000 mPa s (cP). In some embodiments, the viscosity of the first component 3 and second component 4, independently, ranges from 10000 to 30000 mPa s (cP), for example, from 15000 to 25000 mPa s (cP), such as about 20000 mPa s (cP). In some embodiments, the viscosity of the first component 3 and the second component 4 is substantially the same.

By adapting the viscosity of the first component 3 and the second component 4 to be substantially the same, the mixing thereof may be further optimized as the first component 3 and the second component 4 may be released from their respective deformable containers 1, 2 at substantially the same rate.

In embodiments of the invention, not shown in FIG. 1, the device may comprise a first deformable container containing the first component and a second deformable container containing the second component, wherein the device may comprise a third deformable container containing the blowing agent. In some embodiments, the device may comprise a third deformable container containing the blowing agent, and wherein the blowing agent may also be comprised in at least one of the first and second components.

In embodiments of the invention, the second polyorganosiloxane has the following general formula representing a statistical copolymer:

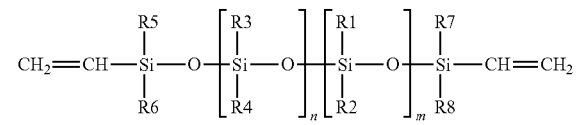

wherein R1 and R2, independently, are selected from monovalent or functionally substituted C4-C12 hydrocarbon group, wherein R3 to R8, independently, are selected from monovalent or functionally substituted C1-C3 hydrocarbon group, wherein n and m indicate the number of repeating units, wherein n and m, independently, are at least one, typically greater than 5. The ratio between the total number of m and n may vary from 1:100 to 40:100.

In embodiments of the invention, R1 and R2, independently, are selected from the group consisting of C5-C12 aryl, preferably phenyl or diphenyl, C4-C12 alkyl, C4-C12 alkenyl, C4-C12 alkynyl, and C4-C12 alkoxy.

In embodiments of the invention, R3 to R8, independently, are selected from the group consisting of C1-C3 alkyl, C2-C3 alkenyl, C2-C3 alkynyl, and C1-C3 alkoxy, preferably methyl, ethyl, propyl, methoxy, ethoxy, propoxy group.

In embodiments of the invention, the ratio between the total number of m and n is from 2:100 to 25:100.

For example, in embodiments of the invention, the second polyorganosiloxane has the following formula representing a statistical copolymer

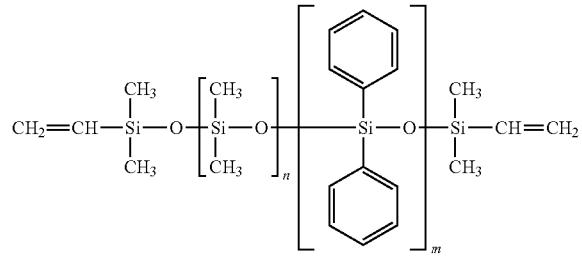

wherein n and m indicate the number of repeating units, wherein n and m, independently, are at least one, typically n may be from 50 to 1500, such as from 500 to 1500, and m may typically be from 5 to 150, such as from 30 to 100, and wherein the ratio between the total number of m and n preferably is from 1:100 to 40:100, for example, from 3:100 to 30:100, such as from 5:100 to 25:100.

As disclosed above, the inventors have realized that in order to ensure a fast curing reaction in the multi-component system it may be advantageous that either (i) the total number of silicon-bonded hydrogen atoms in the multi-component system are in excess of the total number of alkenyl and/or alkynyl groups in the multi-component system, wherein the polyorganosiloxanes comprising the silicon-bonded hydrogen atoms, e.g. the first polyorganosiloxane, preferably have a lower average molecular weight than the polyorganosiloxanes comprising the alkenyl and/or alkynyl groups, e.g. the second polyorganosiloxane; or (ii) the total number of alkenyl and/or alkynyl groups in the multi-component system are in excess of the total number of silicon-bonded hydrogen atoms in the multi-component system, wherein the polyorganosiloxanes comprising the alkenyl and/or alkynyl groups, e.g. the second polyorganosiloxanes, preferably have a lower average molecular weight than the polyorganosiloxanes comprising the silicon-bonded hydrogen atoms, e.g. the first polyorganosiloxane.

Thereby, the smaller polyorganosiloxanes comprising the functional groups in excess have a greater mobility in the reaction mixture of the multi-component system, than the larger polyorganosiloxanes comprising the functional groups in deficit, which overall enhances the reaction rate of the curing reaction.

In embodiments of the invention, the number average molecular weight of the first polyorganosiloxane is less than the number average molecular weight of the second polyorganosiloxane. In embodiments of the invention, the number average molecular weight of the second polyorganosiloxane is less than the number average molecular weight of the first polyorganosiloxane. In embodiments of the invention, the first polyorganosiloxane or the second polyorganosiloxane has a number average molecular weight of 500 to 6000 g/mol, for example, 1000 to 4000 g/mol, such as about 2000 g/mol or about 3000 g/mol. In embodiments of the invention, the first polyorganosiloxane or the second polyorganosiloxane has a number average molecular weight of 10000 to 150000 g/mol, for example, 20000 to 100000 g/mol, such as about 25000 g/mol or 60000 g/mol.

In embodiments of the invention, the first polyorganosiloxane has a number average molecular weight of 500 to 6000 g/mol, and the second polyorganosiloxane has a number average molecular weight of 10000 to 150000 g/mol. Alternatively, in some embodiments, the second polyorganosiloxane has a number average molecular weight of 500 to 6000 g/mol, and the first polyorganosiloxane has a number average molecular weight of 10000 to 150000 g/mol.

In embodiments of the invention, the total number of silicon-bonded hydrogen atoms on each first polyorganosiloxane molecule is from 2 to 50, for example, from 5 to 30.

In embodiments of the invention, the total number of alkenyl and/or alkynyl groups on each second polyorganosiloxane molecule is from 2 to 8, for example, from 2 to 6.

In embodiments of the invention, the ratio between the total number of silicon-bonded hydrogen atoms and the total number of alkenyl and/or alkynyl groups, in the multi-component system, is between 2 and 20, for example, between 4 and 16 or between 6 and 10, such as 8. Alternatively, in embodiments of the invention, the ratio between the total number of alkenyl and/or alkynyl groups and the total number of the silicon-bonded hydrogen atoms, in the multi-component system, is between 2 and 20, for example, between 4 and 16 or between 6 and 10, such as 8.

In addition, to further ensure a fast curing reaction, it is advantageous the multi-component system comprises at least one hydrosilylation catalyst in relatively high concentrations as specified herein.

In embodiments of the invention, the at least one hydrosilylation catalyst comprises a platinum complex.

In some embodiments, the at least one hydrosilylation catalyst comprises a divinyl tetramethyl disiloxane-platinum(0)-complex or a methyl vinyl cyclosiloxane-platinum(0)-complex. In some embodiments the at least one hydrosilylation catalyst further comprises a solvent comprising a vinyl-terminated polydimethyl siloxane, divinyl tetramethyl disiloxane and/or a methyl vinyl cyclosiloxane. In embodiments of the invention, the total concentration of platinum in the in the multi-component system is more than 50 ppm, for example, more than 100 ppm. In some embodiments, the total concentration of platinum in the in the multi-component system ranges from 50 to 300 ppm. In some embodiments, the total concentration of platinum in the in the multi-component system ranges from 50 to 200 ppm, for example, from 50 to 150 ppm or from 100 to 200 ppm. Thereby, a fast curing reaction rate between the first and the second polyorganosiloxane can be facilitated.

Figure 2:
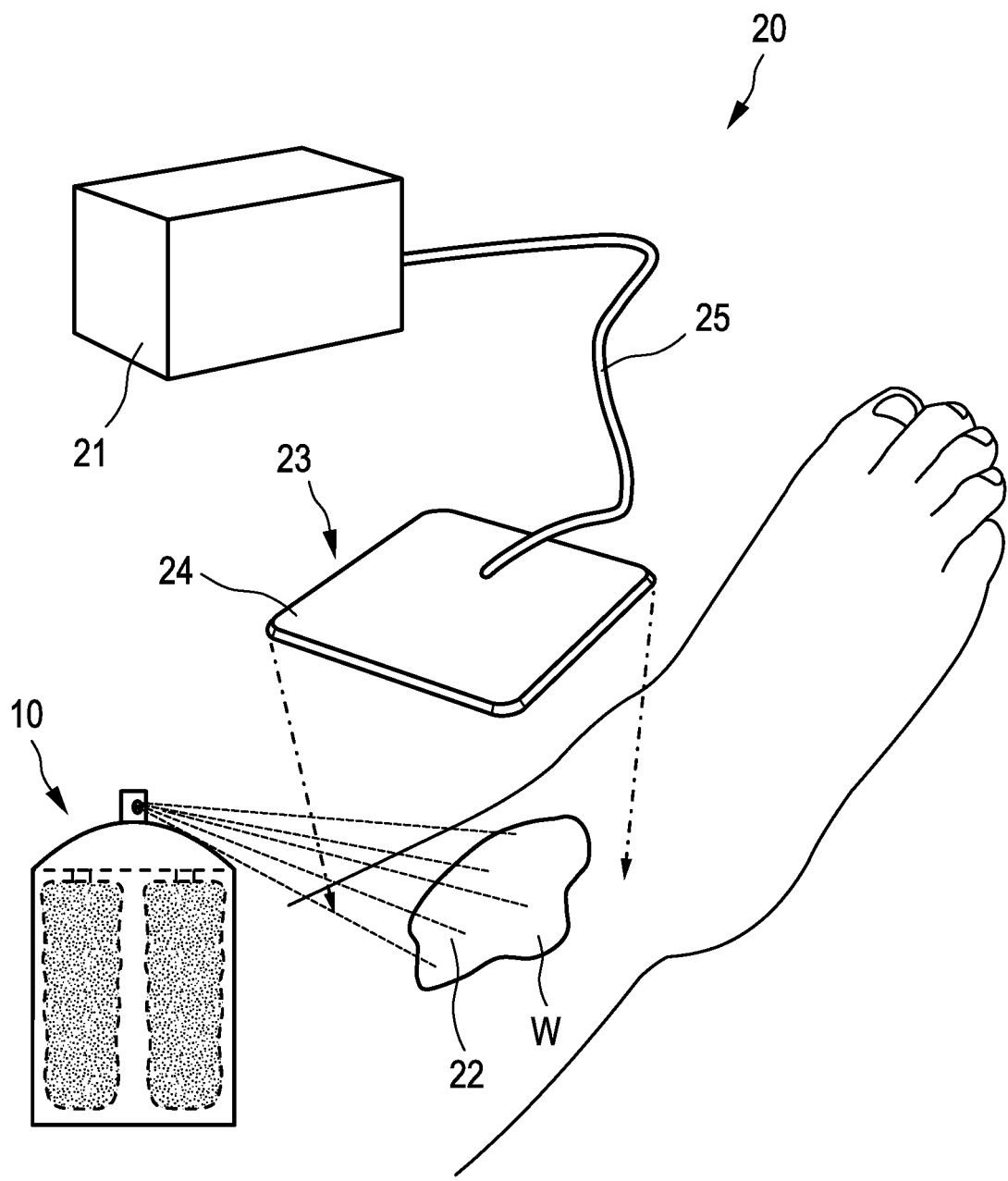
FIG. 2 is a schematic perspective view of an embodiment of a negative pressure wound therapy kit according to the invention.

In embodiments of the invention, the multi-component system or the device comprising the multi-component system is used in wound care. For example, as illustrated in FIG. 2, the multi-component system or the device comprising the multi-component system may be particularly advantageously be used in negative pressure wound therapy. In some embodiments, the multi-component system or the device comprising the multi-component system is used in wound irrigation treatment or in wound instillation treatment.

FIG. 2 illustrates an embodiment of a negative pressure wound therapy kit 20 comprising a negative pressure source 21 for providing negative pressure to a wound W, and the spray dispenser device 10 comprising the multi-component system for providing a silicone foam 22 in the wound cavity W. The negative pressure wound therapy kit 20 further comprises a film dressing 23 comprising a plastic film 24 to be applied on the silicone foam 22 to cover and substantially seal the wound W from surrounding environment. Also included in the kit 20 is a conduit 25 that can be connected, as shown in FIG. 2, to the negative pressure source 21 and to the film dressing 24, thereby providing a negative pressure in and around the wound.

The silicone foam 22 comprises an at least partially open pore structure wherein the density ranges from 0.1 to 0.6 kg/m$^3$, for example from 0.2 to 0.5 kg/m$^3$ or from 0.2 to 0.4 kg/m$^3$, such as about 0.3 kg/m$^3$. When the multi-component system is used in negative pressure therapy it is preferred that at least some amount of liquid is transported through the open-cells in the silicone foam produced from the multi-component system, e.g. that liquid can be transported from a surface facing the wound W to a top surface facing the film dressing 24. For example, the silicone foam may comprise at least one channel from a first external surface of the foam to a second external surface of the silicone foam, wherein the at least one channel comprises a plurality of coherent open cells. In some embodiments, the silicone foam may comprise a surface, e.g. the top surface, wherein no open-cells are present, e.g. a continuous film of cross-linked silicone. Thus, in case the silicone foam is used in negative pressure wound therapy, it may be preferred to make a small cut in the top surface of the silicone foam before or when applying the film dressing on the silicone foam, to thereby expose open-cells on the top surface, and ensure that fluid can go through the silicone foam piece and that a negative pressure can be produced in the silicone foam.

The advantages of the invention have been demonstrated in the following Example.

EXAMPLES

Method of Preparing a Foam Based on the Multi-Component System According to the Present Invention Materials: PLY4-7560 was purchased from NuSil Technology LLC, Catalyst 510 and Crosslinker 110 were purchased from Evonik Hanse GmbH.

Preparation of two silicone mixtures: Using a mechanical rotary mixer, 908 g PLY4-7560 and 92 g Crosslinker 110 were mixed to a homogeneous mixture in a plastic jar. Using the same equipment, 1910 g PLY4-7560 and 90 g of Catalyst 510 were mixed in a second jar.

Preparation of a multicomponent foam producing device: 10 g of the first mixture was transferred to a can (transfer can) and mixed with 10% isobutane. The can was subsequently pressurized using nitrogen gas. 20 g of the second mixture was transferred to a second can and mixed with 10% isobutene. The can was subsequently pressurized using nitrogen gas. Using the pressure in both transfer cans, the silicone mixtures from the cans were transferred into two separate containers in a pre-pressurized (with nitrogen gas) final container.

Preparation of a foam using the multicomponent device: The final container was equipped with an actuator connected to a static mixer. By pressing the actuator the two mixtures were allowed to enter the static mixer, mix, and finally exit the multicomponent device into a jar for subsequent foaming and curing. After approx. 5 minutes, the foam was removed from the jar.

Method of Preparing a Colored Foam Based on the Multi-Component System According to the Present Invention Materials: PLY4-7560, MED-4900-5 (yellow-colored first component) and MED-4900-7 (blue-colored second component) were purchased from NuSil Technology LLC. Catalyst 510 and Crosslinker 110 were purchased from Evonik Hanse GmbH.

Preparation of two siloxane mixtures: Using a speed mixer, 90.8 g PLY4-7560, 9.2 g Crosslinker 110 and 2.0 g MED-4900-5 were mixed to a homogeneous yellow-colored mixture in a plastic jar. Using the same equipment, 191.0 g PLY4-7560, 9.0 g Catalyst 510 and 4.0 g MED-4900-7 were mixed to a homogeneous blue-colored mixture in a second jar.

Preparation of a green-colored cured silicone material: approximately 2 g of the yellow-colored siloxane mixture and 4 g of the yellow-colored siloxane mixture, were transferred to a two-compartment syringe equipped with a plunger and static mixer to simulate a pressurized can. The plunger was pressed down manually and the two siloxane components were mixed through the static mixer and exiting the device as a homogeneous green-colored silicone mixture, which no discernible effect of the dyestuff present.

Method of Measuring Density of the Silicone Foam

A small piece of the foam (approx. 1×3×5 cm) was weighed (4.13 g) and placed into a 100 mL measuring cylinder. A known volume (50 mL) of spherical metallic beads (d=2 mm) were added to the measuring cylinder, completely surrounding the foam. The foam volume (15 cm$^3$) was obtained by the subtraction $V_{foam+particles} - V_{particles}$, giving a foam density of 0.3 g/cm$^3$.

The invention claimed is:

1. A multi-component system for producing a silicone foam, said system comprising: a first component comprising a first polyorganosiloxane, said first polyorganosiloxane comprising at least two silicon-bonded hydrogen atoms; a second component comprising a second polyorganosiloxane, said second polyorganosiloxane comprising at least two alkenyl- and/or alkynyl groups, and at least one hydrosilylation catalyst; said multi-component system further comprising at least one blowing agent, wherein said second polyorganosiloxane has the following general formula, representing a statistical co-polymer $$R10-\underset{R6}{\overset{R5}{\underset{|}{\overset{|}{Si}}}}-O-\left[\underset{R4}{\overset{R3}{\underset{|}{\overset{|}{Si}}}}-O\right]_n\left[\underset{R2}{\overset{R1}{\underset{|}{\overset{|}{Si}}}}-O\right]_m\underset{R8}{\overset{R7}{\underset{|}{\overset{|}{Si}}}}-R9$$

wherein R1 is selected from monovalent or functionally substituted C4-C12 hydrocarbon group, wherein R2 is selected from monovalent or functionally substituted C1-C12 hydrocarbon group, wherein R3 to R10, independently, are selected from monovalent or functionally substituted C1-C3 hydrocarbon groups, and wherein at least one of R3 to R10 is a C2-C3 alkenyl or C2-C3 alkynyl, wherein n and m indicate the number of repeating units, and wherein the ratio between the total number of m and n is from 1:100 to 40:100.

2. The multi-component system according to claim 1, wherein R10 and R9 is a C2-C3 alkenyl or C2-C3 alkynyl, and wherein R1 and R2, independently, are selected from monovalent or functionally substituted C4-C12 hydrocarbon group.

3. The multi-component system according to claim 1, wherein R1 and R2 are independently selected from the group consisting of C5-C12 aryl, preferably phenyl or diphenyl, C4-C12 alkyl, C4-C12 alkenyl, C4-C12 alkynyl, and C4-C12 alkoxy.

4. The multi-component system according to claim 1, wherein R3 to R8 are independently selected from the group consisting of C1-C3 alkyl, C2-C3 alkenyl, C2-C3 alkynyl, and C1-C3 alkoxy, preferably methyl, ethyl, propyl, methoxy, ethoxy, propoxy group.

5. The multi-component system according to claim 1, wherein R3 to R8 are methyl, and wherein R1 and R2 are phenyl.

6. The multi-component system according to claim 1, wherein the ratio between the total number of m and n is from 2:100 to 25:100.

7. The multi-component system according to claim 1, wherein the ratio between the total number of silicon-bonded hydrogen atoms and the total number of alkenyl and/or alkynyl groups, in the multi-component system, is between 2 and 20.

8. The multi-component system according to claim 7, wherein the number average molecular weight of the first polyorganosiloxane is lower than the number average molecular weight of the second polyorganosiloxane.

9. The multi-component system according to claim 1, wherein the ratio between the total number of alkenyl and/or alkynyl groups and the total number of the silicon-bonded hydrogen atoms, in the multi-component system, is between 2 and 20.

10. The multi-component system according to claim 9, wherein the number average molecular weight of the second polyorganosiloxane is lower than the number average molecular weight of the first polyorganosiloxane.

11. The multi-component system according to claim 1, wherein said blowing agent is selected from the group consisting of propane, butane, isobutane, isobutene, isopentane, dimethylether or mixtures thereof.

12. The multi-component system according to claim 1, wherein the blowing agent is the main source for gas that leads to the formation of foam, in particular wherein the reaction between the first component and the second component essentially does not lead to the production of gas that leads to the formation of foam.

13. The multi-component system according to claim 1, wherein said first and/or said second component further comprises at least one colloidal silica or pyrogenic silica.

14. The multi-component system according to claim 1, wherein said first component further comprises said second polyorganosiloxane.

15. The multi-component system according to claim 1, wherein at least one dyestuff is added to the first and second component, respectively, wherein the at least one dyestuff for the first component is of different color compared to the at least one dyestuff of the second component.

16. A device for producing a foam comprising:
the multi-component system according to claim 1;
at least one means for bringing said first component and said second component into contact with each other, wherein said first component and said second component are contained separately.

17. The device according to claim 16 wherein said device comprises a first deformable container containing said first component and a second deformable container containing said second component, preferably wherein the means for bringing said first component and said second component into contact with each other is a propellant gas.

18. A silicone foam obtained from the multi-component system according to claim 1.

19. The silicone foam according to claim 18, wherein said silicone foam has a density of less than 0.7 kg/m$^3$.

20. A negative pressure wound therapy kit comprising:
a negative pressure source for providing negative pressure to a wound;
a multi-component system according to claim 1 for providing a silicone foam in a wound cavity;
a film dressing comprising a plastic film to be applied on said silicone foam, to cover and substantially seal the wound from surrounding environment.

21. A method of treating a wound comprising a wound cavity comprising the step of:
providing a multi-component system according to claim 1;
in-situ producing and curing a silicone foam within said wound cavity having an entire area such that said produced silicone foam is in physical contact with substantially the entire area of the wound cavity;
providing a film dressing on a top surface of said silicone foam and on skin surrounding said wound, to thereby provide a substantially air-tight seal over the wound;
providing a negative pressure source for providing negative pressure to the wound;
providing a conduit configured to transmit negative pressure from said negative pressure source to said film dressing; and
connecting said conduit to said negative pressure source.

22. A method of treating a wound according to claim 21, wherein the silicone foam is produced essentially with the blowing agent that is part of the multi-component system and essentially without any gas formed as a result of the reaction between said first component and said second component.

* * * * *